(12) United States Patent
Yang

(10) Patent No.: US 8,917,941 B2
(45) Date of Patent: Dec. 23, 2014

(54) SYSTEM AND METHOD FOR SHAPE MEASUREMENTS ON THICK MPR IMAGES

(75) Inventor: Lining Yang, East Windsor, NJ (US)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 13/244,984

(22) Filed: Sep. 26, 2011

(65) Prior Publication Data

US 2013/0208989 A1 Aug. 15, 2013

Related U.S. Application Data

(60) Provisional application No. 61/387,182, filed on Sep. 28, 2010.

(51) Int. Cl.
| | |
|---|---|
| *G06K 9/00* | (2006.01) |
| *G06K 9/52* | (2006.01) |
| *A61B 6/03* | (2006.01) |
| *A61B 6/00* | (2006.01) |
| *G01R 33/56* | (2006.01) |
| *G06T 7/60* | (2006.01) |
| *A61B 8/08* | (2006.01) |

(52) U.S. Cl.
CPC .. *G06K 9/52* (2013.01); *G06K 9/00* (2013.01); *A61B 6/03* (2013.01); *A61B 6/5211* (2013.01); *G01R 33/5608* (2013.01); *G06T 7/602* (2013.01); *A61B 8/5215* (2013.01); *G06T 2207/10081* (2013.01); *G06T 2207/30004* (2013.01)
USPC ........... 382/203; 382/145; 345/424; 345/505; 345/536

(58) Field of Classification Search
CPC ........ A61B 6/03; A61B 6/5211; A61B 6/032; A61B 8/5215; G01R 33/48; G01R 33/5608; G06T 2207/10081; G06T 2207/30004; G06T 2207/10104; G06T 11/005; G06T 7/602; G06T 2207/10088; G06T 2207/10116; G06K 9/52; G01N 21/956; G06M 11/02
USPC .................. 382/145, 203; 345/424, 505, 536
See application file for complete search history.

(56) References Cited

U.S. PATENT DOCUMENTS

| | | | | |
|---|---|---|---|---|
| 3,503,043 | A * | 3/1970 | Brass | 382/203 |
| 3,829,838 | A * | 8/1974 | Lewis et al. | 345/419 |
| 5,317,689 | A * | 5/1994 | Nack et al. | 345/505 |
| 5,546,807 | A * | 8/1996 | Oxaal et al. | 73/606 |
| 5,598,345 | A * | 1/1997 | Tokura | 382/150 |
| 5,694,481 | A * | 12/1997 | Lam et al. | 382/145 |
| 6,640,000 | B1 * | 10/2003 | Fey et al. | 382/128 |
| 6,870,949 | B2 * | 3/2005 | Baldwin | 382/145 |
| 6,891,966 | B2 * | 5/2005 | Chen | 382/145 |
| 7,935,055 | B2 * | 5/2011 | Burckhardt | 600/300 |

(Continued)

*Primary Examiner* — Vu Le
*Assistant Examiner* — Aklilu Woldemariam

(57) ABSTRACT

A method for measuring shapes in thick multi-planar reformatted (MPR) digital images, including identifying a shape in a digital MPR image, scan-converting points corresponding to the identified shape on a starting plane of an MPR slab in an image volume from which the MPR was obtained to generate a plurality of starting points for the identified shape, calculating an end point in the MPR slab corresponding to each starting point, propagating a ray from each starting point to each corresponding end point, accumulating samples along each ray, and computing a desired measurement value from the accumulated samples after reaching the end point for all rays.

20 Claims, 4 Drawing Sheets

(56) References Cited

U.S. PATENT DOCUMENTS

| | | | |
|---|---|---|---|
| 2002/0176535 A1* | 11/2002 | Dixon et al. | 378/62 |
| 2005/0113679 A1* | 5/2005 | Suryanarayanan et al. | 600/425 |
| 2007/0116357 A1* | 5/2007 | Dewaele | 382/173 |
| 2007/0206008 A1* | 9/2007 | Kaufman et al. | 345/424 |
| 2008/0123923 A1* | 5/2008 | Gielen et al. | 382/131 |
| 2008/0266293 A1* | 10/2008 | Cohen | 345/424 |
| 2008/0317310 A1* | 12/2008 | Suresh et al. | 382/130 |
| 2008/0317314 A1* | 12/2008 | Schwartz et al. | 382/131 |

\* cited by examiner

SYSTEM AND METHOD FOR SHAPE MEASUREMENTS ON THICK MPR IMAGES

CROSS REFERENCE TO RELATED UNITED STATES APPLICATIONS

This application claims priority from "Method and Apparatus for Shape Measurement on Thick MPR image", U.S. Provisional Application No. 61/387,182 of Lining Yang, filed Sep. 28, 2010, the contents of which are herein incorporated by reference in their entirety.

TECHNICAL FIELD

This disclosure is directed to methods for automatically measuring shapes in thick multi-planar reformatted digital images.

DISCUSSION OF THE RELATED ART

Multi-planar reconstruction (MPR) is a simple method of constructing an image volume from a series of 2D images, such as those acquired through X-ray computed tomography, magnetic resonance imaging, etc. An image volume is built by stacking the series of 2D images, after which slices may be cut through the volume in a different plane. Special projection methods, such as maximum-intensity projection (MIP) or minimum-intensity projection (mIP), can be used to render the reconstructed volume. Modern software allows reconstruction in non-orthogonal (oblique) planes so that an optimal plane can be chosen to display an anatomical structure.

Shape measurement is very important in Medical Imaging. A user can draw a circle or arbitrary freehand polygon on a Multi-Planar Reformatted (MPR) image and obtain intensity values and/or the area of the region included in the shape. The user expects to obtain measurement results that correspond to what is observed in the rendered image on the display. For a thin MPR, which includes only one slice in the rendering result, there is no ambiguity between the measurements and the observed shape. However, for the thick MPR case, which renders a thick slab that may include multiple slices, what to measure becomes a question. A user also expects the result to remain the same when zooming in and out. Performing real time editing and moving of the shape object, requires high speed measurements.

SUMMARY

Exemplary embodiments of the invention as described herein generally include methods and systems for automatically measuring shapes in thick multi-planar reformatted digital images.

According to an aspect of the invention, there is provided a method for measuring shapes in thick multi-planar reformatted (MPR) digital images, including identifying a shape in a digital MPR image, scan-converting points corresponding to the identified shape on a starting plane of an MPR slab in an image volume from which the MPR was obtained to generate a plurality of starting points for the identified shape, calculating an end point in the MPR slab corresponding to each starting point, propagating a ray from each starting point to each corresponding end point, accumulating samples along each ray, and computing a desired measurement value from the accumulated samples after reaching the end point for all rays.

According to a further aspect of the invention, samples are accumulated by performing tri-linear interpolation at each sample point.

According to a further aspect of the invention, samples are accumulated by performing nearest-neighbor interpolation at each sample point.

According to a further aspect of the invention, accumulating samples includes averaging the sample values.

According to a further aspect of the invention, accumulating samples comprises saving a maximum of the accumulated samples.

According to a further aspect of the invention, calculating an end point corresponding to each starting point comprises extending a normal of the MPR slab from each starting point until an end plane of the MPR slab is reached in the image volume, where the end point corresponds to a point of intersection of the extended normal and the end plane of the MPR slab.

According to a further aspect of the invention, calculating an end point corresponding to each starting point comprises extending a normal of the MPR slab from each starting point fro a distance corresponding to a thickness of the slab, where an end point of the extended normal is the end point corresponding to the starting point.

According to a further aspect of the invention, the method includes saving the sample accumulated for each ray, where the measurement values are computed from the saved accumulated samples.

According to a further aspect of the invention, computing a desired measurement value from the accumulated samples comprises applying an MPR filter to the accumulated samples.

According to a further aspect of the invention, computing a desired measurement value from the accumulated samples comprises applying maximum intensity filter to the accumulated samples.

According to another aspect of the invention, there is provided a method for measuring shapes in thick multi-planar reformatted (MPR) digital images, including identifying a shape in a digital MPR image, scan-converting points corresponding to the identified shape on a starting plane of an MPR slab in an image volume from which the MPR was obtained to generate a plurality of starting points for the identified shape, calculating an end point in the MPR slab corresponding to each starting point, propagating a ray from each starting point to each corresponding end point, accumulating samples along each ray, and saving the sample accumulated for each ray.

According to a further aspect of the invention, the method includes computing a desired measurement value from the saved accumulated samples after reaching the end point for all rays.

According to another aspect of the invention, there is provided a non-transitory program storage device readable by a computer, tangibly embodying a program of instructions executed by the computer to perform the method steps for measuring shapes in thick multi-planar reformatted (MPR) digital images.

DETAILED DESCRIPTION OF EXEMPLARY EMBODIMENTS

Figure 1:
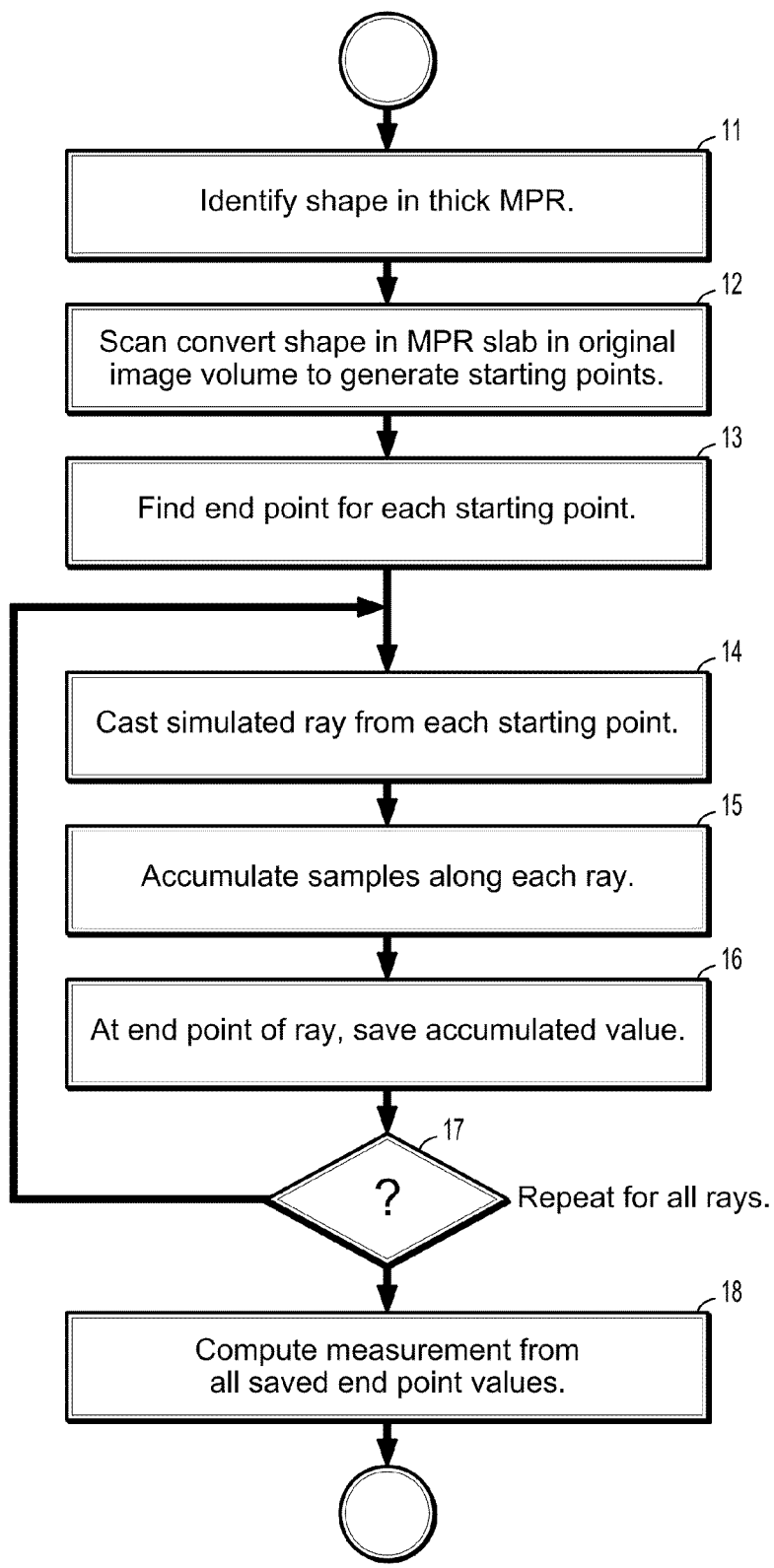
FIG. 1 is a flowchart of an algorithm to automatically measuring a shape in a thick multi-planar reformatted (MPR) image, according to an embodiment of the invention.

Exemplary embodiments of the invention as described herein generally include systems and methods for automatically measuring a shape in a thick multi-planar reformatted (MPR) image. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-dimensional images and voxels for 3-dimensional images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, the methods of the inventions are not limited to such images, and can be applied to images of any dimension, e.g., a 2-dimensional picture or a 3-dimensional volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

There are two general approaches to measuring shapes in thick MPRs. A first approach measures the original volume, with the shape as a constraint. The other approach measures the shape in the rendered thick MPR. In particular, the image is first rendered, the shape is applied on the rendered image, and the measurement result is obtained from the shape on the image. There are issues associated with each approach.

The first approach uses 3D scan conversion methods which scan convert the voxels enclosed in a shape identified in the image and produce the measurement result. However, the results may appear confusing when compared to the rendered image shown on a display screen. As is known, MPR essentially averages all slices in a thick slab and displays the averaged result. If, in a thick MPR slab, there are regions of high intensity surrounded by low intensity regions, then, after averaging, the rendered image will show semi-high intensity results. However, the first measuring approach will usually yield very high-intensity measurement results, which may seem confusing to the user.

The second approach addresses this issue by being essentially a "what you measure is what you see" approach. The measurement actually occurs in the already rendered MPR image. However, if a user zooms in or out of the MPR image, the measurement results may change although the shape does not actually change. This is due to the fact that the MPR process performs tri-linear interpolation of each sample first and then performs the averaging operation. Zooming-in or out will result in different tri-linearly interpolated samples. Since the second approach performs the measurement operation on the rendered image, it will also obtain different measurement results accordingly. One way to address this issue is the render two images, one for the image shown on a display screen and the other for measurement purposes only. The second image will be rendered with a fixed zoom factor regardless of the zoom factor used to produce the first image, which is shown on the display screen. However, a user may want to edit the shape object by dragging the shape object around the image or enlarging or shrinking the shape on the fly. Thus, performance needs to be considered, especially for the shape measurement of very thick MPR images. In addition, rendering two thick MPRs can be too slow for real time shape editing.

A novel method according to an embodiment of the invention which combines the strengths of both of the aforementioned approaches uses the "what you measure is what you see" feature of the second approach but avoids the measurement results changes that occur due to zooming. FIG. 1 is a flowchart of a shape measuring algorithm according to an embodiment of the invention. An algorithm begins at step 11 by identifying a shape on a thick MPR image. An exemplary, non-limiting method of identifying a shape is for the user to draw the shape, such as a circle or polygon, on the displayed image. In an algorithm according to an embodiment of the invention, the measurement is not performed on the rendered image. Instead, referring now to the figure, the shape identified in the rendered image, such as a polygon or a circle, is scan converted at step 12 on the starting plane of the thick MPR slab in the original image volume. Each scan converted point within the shape may be considered as a starting point. An end point corresponding to each starting point may be found at step 13 by following the slab's normal direction using the thickness of the slab or knowledge of the ending plane of the MPR slab. At step 14, with the calculated starting and ending points, ray casting may be simulated to propagate a ray from each starting point to each corresponding end point. Samples are accumulated along each ray at step 15. According to an embodiment of the invention, tri-linear interpolation is performed for each sample along each ray. The nature of the accumulated sample may vary depending on the type of projection. For example, if the projection is a maximum/minimum intensity projection, the minimum or maximum values of the samples are saved. On the other hand, for an MPR, the samples are accumulated and averaged. Other types of sample processing are also within the scope of other embodiments of the invention. At the end of the ray, at step 16, the accumulated sample value for the corresponding starting point is saved. This ray casting and measuring is repeated from step 17 for all points in the scan converted shape on the starting slice of the MPR slab. At step 18, after samples have been accumulated and saved for all rays, the final measurement result is obtained as a function of the saved values. The application that calls the measurement operation can access saved values and calculate whatever is needed, such as a minimum value, a maximum value, an average value with a standard deviation, etc., of the values for all end points.

Compared to the two aforementioned algorithms, a method according to an embodiment of the invention ensures a user that what is measured corresponds to what is seen. However measurement results it will not change when the zoom factor changes. Also a method according to an embodiment of the invention does not require the rendering of a second image to ensure an unchanged measurement with a zoom factor change. Since a user typically only measures a small region which results in a small shape measurement, the number of rays propagated through the slab in an algorithm a method according to an embodiment of the invention is relatively few as compared to the number of rays required for an entire slab, thus performance is relatively fast.

In a case where a user wants not only intensity measurement results but also the number of voxels included in the shape object on the MPR slab, an algorithm according to an embodiment of the invention can be adapted by using a nearest neighbor interpolation along the ray instead of the trilinear interpolation of the ray to therefore collect all voxels encountered along each ray propagated from each starting point of the scan converted shape result on the starting plane of the MPR slab.

Tests of an algorithm according to an embodiment of the invention have essentially met users' expectations that what one sees is what one gets, and produces measurement results that are invariant with respect to changes of the zoom factor. Moreover, the performance is such that a user can move and edit a shape measurement on the fly without any major delay.

Figure 3A:
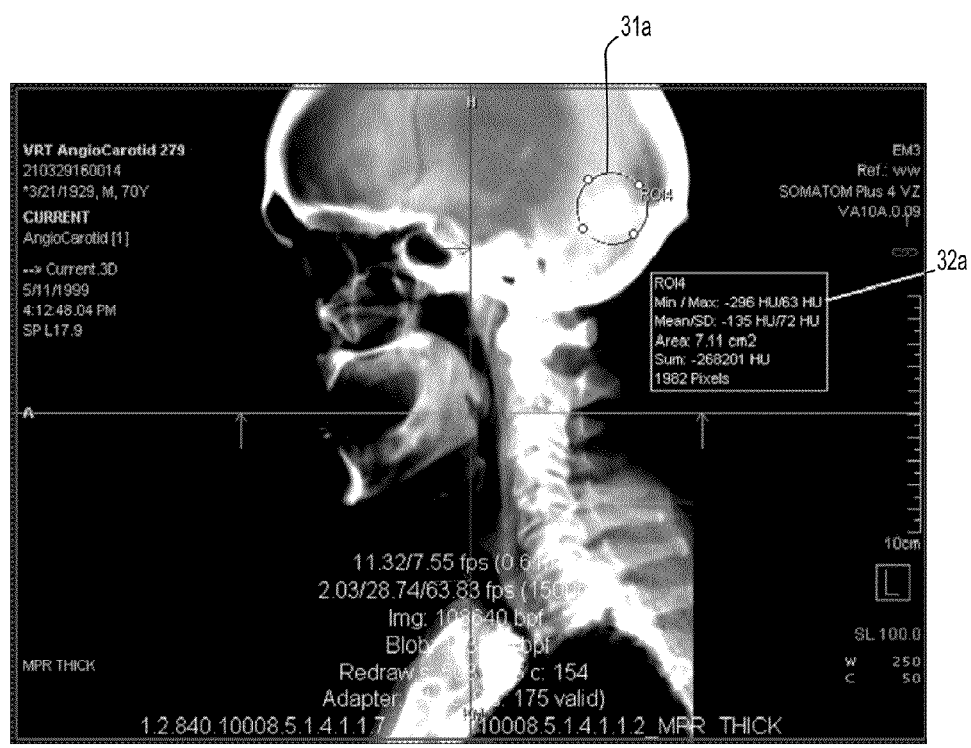
FIGS. 3A-B are two images of measurement results, one using a freehand polygon and the other using a circle, according to an embodiment of the invention.
Figure 3B:
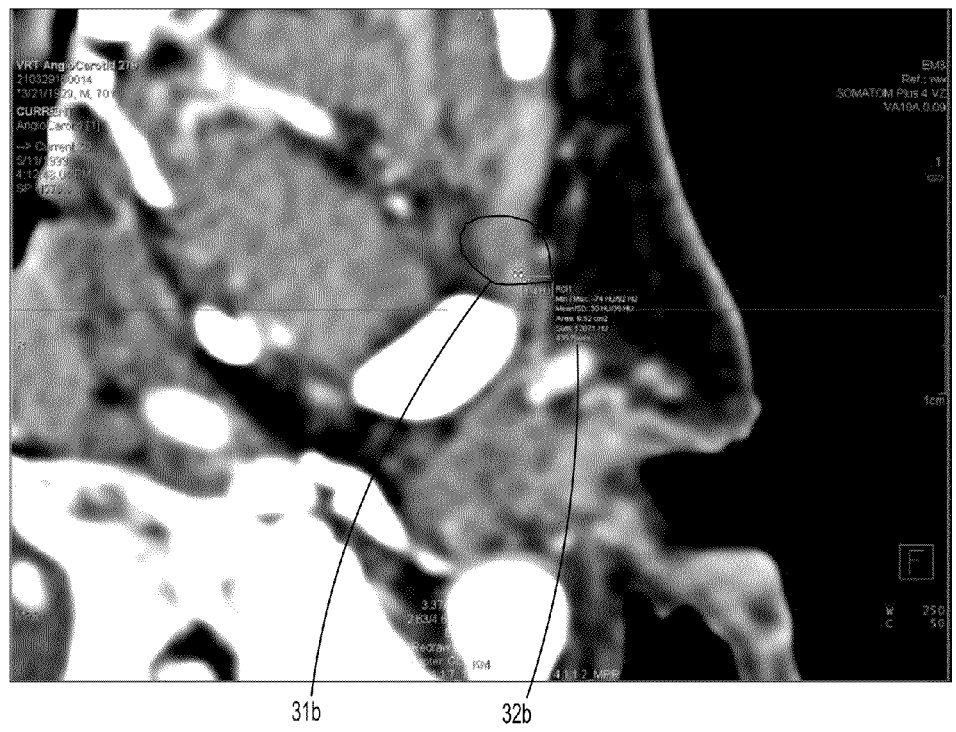

FIGS. 3A-B are two MPR images with measurement results, generated from a computed tomography (CT) image, according to an embodiment of the invention. FIG. 3A depicts a circular region 31a with measurement results 32a. The measurement results include the minimum and maximum pixel intensities (−296 HU/63 HU), the mean intensity and its standard deviation (−135 HU/72 HU), the area (7.11 cm$^2$, 1982 pixels), and the intensity sum (−268201 HU). FIG. 3B depicts a hand drawn polygonal region 31b with measurement results 32b. The measurement results include the minimum and maximum pixel intensities (−74 HU/92 HU), the mean intensity and its standard deviation (30 HU/39 HU), the area (0.52 cm$^2$, 435 pixels), and intensity sum (13071 HU).

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 2:
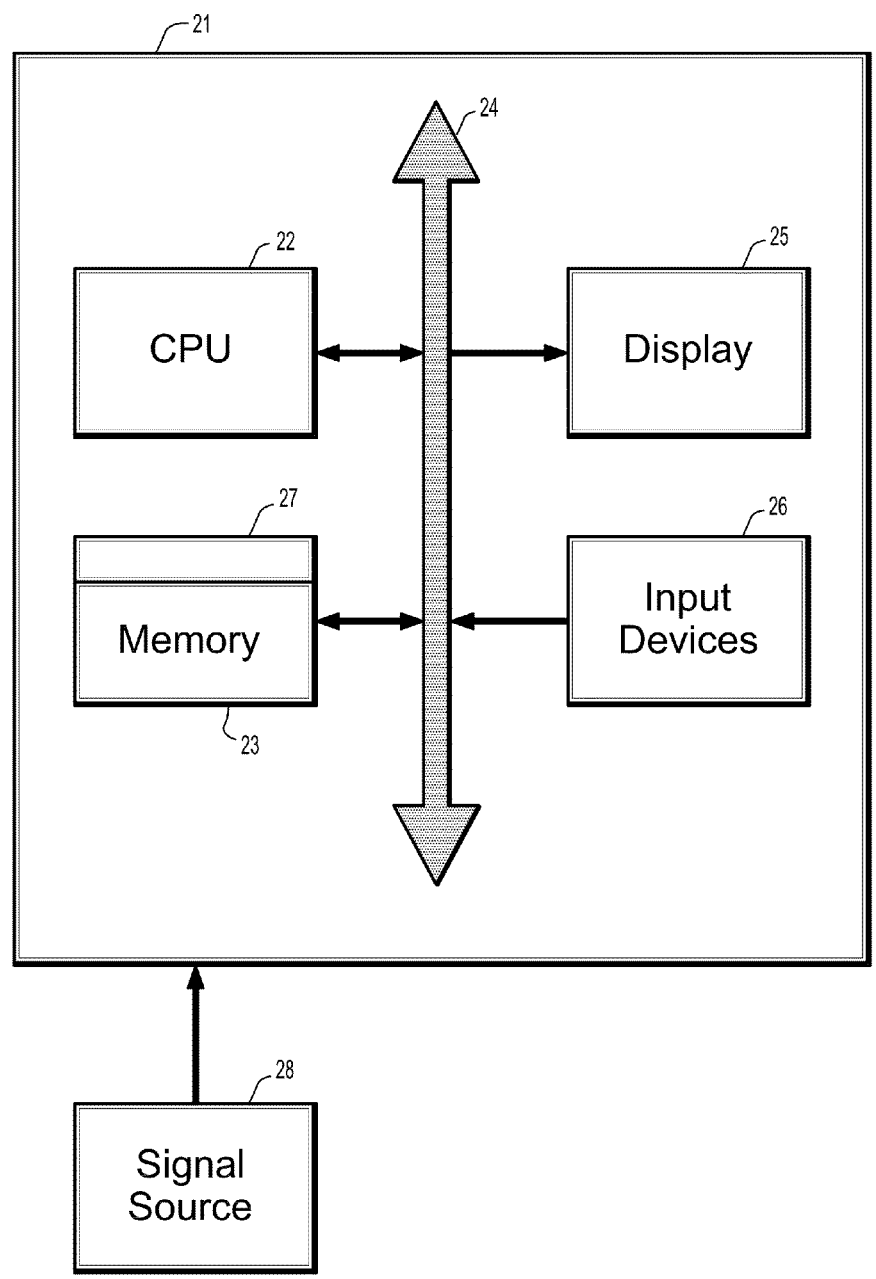
FIG. 2 is a block diagram of an exemplary computer system for implementing a method for automatically measuring a shape in a thick multi-planar reformatted (MPR) image, according to an embodiment of the invention.

FIG. 2 is a block diagram of an exemplary computer system for implementing a method for automatically measuring a shape in a thick multi-planar reformatted (MPR) image, according to an embodiment of the invention. Referring now to FIG. 2, a computer system 21 for implementing the present invention can comprise, inter alia, a central processing unit (CPU) 22, a memory 23 and an input/output (I/O) interface 24. The computer system 21 is generally coupled through the I/O interface 24 to a display 25 and various input devices 26 such as a mouse and a keyboard. The support circuits can include circuits such as cache, power supplies, clock circuits, and a communication bus. The memory 23 can include random access memory (RAM), read only memory (ROM), disk drive, tape drive, etc., or a combinations thereof. The present invention can be implemented as a routine 27 that is stored in memory 23 and executed by the CPU 22 to process the signal from the signal source 28. As such, the computer system 21 is a general purpose computer system that becomes a specific purpose computer system when executing the routine 27 of the present invention.

The computer system 21 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to exemplary embodiments, those skilled in the art will appreciate that various modifications and substitutions can be made thereto without departing from the spirit and scope of the invention as set forth in the appended claims.

What is claimed is:

1. A method for measuring shapes in thick multi-planar reformatted (MPR) digital images, comprising the steps of:
    automatically measuring a shape in a digital MPR image;
    scan-converting points corresponding to the identified shape on a starting plane of a thick MPR slab in an image volume from which the MPR was obtained to generate a plurality of starting points for the identified shape, wherein the thick MPR slab comprises a plurality of slices;
    calculating an end point in the MPR slab corresponding to each starting point, wherein calculating an end point corresponding to each starting point comprises extending a normal of the MPR slab from each starting point until an end plane of the MPR slab is reached in the image volume, wherein the end point corresponds to a point of intersection of the extended normal and the end plane of the MPR slab;
    propagating a ray from each starting point to each corresponding end point;
    accumulating samples along each ray; and
    computing a desired measurement value from the accumulated samples after reaching the end point for all rays,
    wherein the steps of automatically measuring a shape, scan-converting points, calculating an end point, propagating a ray, accumulating samples, and computing a desired measurement value are performed by a computer processor.

2. The method of claim 1, wherein samples are accumulated by performing tri-linear interpolation at each sample point.

3. The method of claim 1, wherein samples are accumulated by performing nearest-neighbor interpolation at each sample point.

4. The method of claim 1, wherein accumulating samples includes averaging the sample values.

5. The method of claim 1, wherein accumulating samples comprises saving a maximum of the accumulated samples.

6. The method of claim 1, wherein calculating an end point corresponding to each starting point comprises extending a normal of the MPR slab from each starting point fro a distance corresponding to a thickness of the slab, wherein an end point of the extended normal is the end point corresponding to the starting point.

7. The method of claim 1, further comprising saving the sample accumulated for each ray, wherein the measurement values are computed from the saved accumulated samples.

8. The method of claim 1, wherein computing a desired measurement value from the accumulated samples comprises applying an MPR filter to the accumulated samples.

9. The method of claim 1, wherein computing a desired measurement value from the accumulated samples comprises applying maximum intensity filter to the accumulated samples.

10. A method for measuring shapes in thick multi-planar reformatted (MPR) digital images, comprising the steps of:
automatically measuring a shape in a digital MPR image;
scan-converting points corresponding to the identified shape on a starting plane of a thick MPR slab in an image volume from which the MPR was obtained to generate a plurality of starting points for the identified shape, wherein the thick MPR slab comprises a plurality of slices;
calculating an end point in the MPR slab corresponding to each starting point, wherein calculating an end point corresponding to each starting point comprises extending a normal of the MPR slab from each starting point fro a distance corresponding to a thickness of the slab, wherein an end point of the extended normal is the end point corresponding to the starting point;
propagating a ray from each starting point to each corresponding end point;
accumulating samples along each ray; and
saving the sample accumulated for each ray,
wherein the steps of automatically measuring a shape, scan-converting points, calculating an end point, propagating a ray, accumulating samples, and saving the sample are performed by a computer processor.

11. The method of claim 10, further comprising computing a desired measurement value from the saved accumulated samples after reaching the end point for all rays.

12. A non-transitory program storage device readable by a computer, tangibly embodying a program of instructions executed by the computer to perform the method steps for measuring shapes in thick multi-planar reformatted (MPR) digital images, the method comprising the steps of:
automatically measuring a shape in a digital MPR image;
scan-converting points corresponding to the identified shape on a starting plane of a thick MPR slab in an image volume from which the MPR was obtained to generate a plurality of starting points for the identified shape, wherein the thick MPR slab comprises a plurality of slices;
calculating an end point in the MPR slab corresponding to each starting point, wherein calculating an end point corresponding to each starting point comprises extending a normal of the MPR slab from each starting point until an end plane of the MPR slab is reached in the image volume, wherein the end point corresponds to a point of intersection of the extended normal and the end plane of the MPR slab;
propagating a ray from each starting point to each corresponding end point;
accumulating samples along each ray; and
computing a desired measurement value from the accumulated samples after reaching the end point for all rays.

13. The computer readable program storage device of claim 12, wherein samples are accumulated by performing tri-linear interpolation at each sample point.

14. The computer readable program storage device of claim 12, wherein samples are accumulated by performing nearest-neighbor interpolation at each sample point.

15. The computer readable program storage device of claim 12, wherein accumulating samples includes averaging the sample values.

16. The computer readable program storage device of claim 12, wherein accumulating samples comprises saving a maximum of the accumulated samples.

17. The computer readable program storage device of claim 12, wherein calculating an end point corresponding to each starting point comprises extending a normal of the MPR slab from each starting point fro a distance corresponding to a thickness of the slab, wherein an end point of the extended normal is the end point corresponding to the starting point.

18. The computer readable program storage device of claim 12, the method further comprising saving the sample accumulated for each ray, wherein the measurement values are computed from the saved accumulated samples.

19. The computer readable program storage device of claim 12, wherein computing a desired measurement value from the accumulated samples comprises applying an MPR filter to the accumulated samples.

20. The computer readable program storage device of claim 12, wherein computing a desired measurement value from the accumulated samples comprises applying maximum intensity filter to the accumulated samples.

* * * * *